US011607350B2

(12) United States Patent
Morimoto et al.

(10) Patent No.: US 11,607,350 B2
(45) Date of Patent: *Mar. 21, 2023

(54) WEARABLE ARTICLE HAVING ELASTIC BELT

(71) Applicant: The Procter & Gamble Company, Cincinnati, OH (US)

(72) Inventors: Koichi Morimoto, Beijing (CN); Ling Tong, Beijing (CN); Chunmin Cheng, Beijing (CN); Masaharu Nishikawa, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 535 days.

This patent is subject to a terminal disclaimer.

(21) Appl. No.: 16/806,348

(22) Filed: Mar. 2, 2020

(65) Prior Publication Data

US 2020/0197234 A1 Jun. 25, 2020

Related U.S. Application Data

(63) Continuation of application No. 15/424,117, filed on Feb. 3, 2017, now Pat. No. 10,624,797, which is a
(Continued)

(51) Int. Cl.
*A61F 13/49* (2006.01)
*A61F 13/496* (2006.01)

(52) U.S. Cl.
CPC ...... *A61F 13/49011* (2013.01); *A61F 13/496* (2013.01); *A61F 13/49014* (2013.01);
(Continued)

(58) Field of Classification Search
CPC .......... A61F 13/49011; A61F 13/49014; A61F 13/496; A61F 2013/49025; A61F 2013/49026

See application file for complete search history.

(56) References Cited

U.S. PATENT DOCUMENTS

| 2,462,195 A | 2/1949 | Jacobson |
| 2,513,039 A | 6/1950 | Miller |

(Continued)

FOREIGN PATENT DOCUMENTS

| CN | 2167695 | 8/1994 |
| CN | 1246324 | 8/2000 |

(Continued)

OTHER PUBLICATIONS

International Search Report and Written Opinion; Application Ser. No. PCT/CN2014/085245, dated May 26, 2015, 9 pages.
(Continued)

*Primary Examiner* — Susan S Su
(74) *Attorney, Agent, or Firm* — Charles R. Matson; Richard L. Alexander

(57) ABSTRACT

An article with the entirety of the length of the belt side edge of the front belt seamed with a certain length of the belt side edge of the back belt to define a seam length LS. The front and back belts may each be divided into 4 zones extending in the transverse direction and defined by its location from the distal edge to the proximal edge relative to the percentage of the seam length LS where: 0-25% is the waist zone, 25-50% is the distal tummy zone, 50-85% is the proximal tummy zone, and 85-100% is the leg zone. The tensile stress of the front leg zone may be no more than 50% of the tensile stress of the front proximal tummy zone, and the tensile stress of the back leg zone may be no more than 100% of the tensile stress of the back proximal tummy zone.

20 Claims, 8 Drawing Sheets

Related U.S. Application Data continuation of application No. PCT/CN2015/072193, filed on Feb. 4, 2015, and a continuation-in-part of application No. PCT/CN2014/085245, filed on Aug. 27, 2014.

(52) U.S. Cl.
CPC ............... *A61F 2013/49025* (2013.01); *A61F 2013/49026* (2013.01)

(56) References Cited

U.S. PATENT DOCUMENTS

| | | | |
|---|---|---|---|
| 2,632,177 A | 3/1953 | Bigger | |
| 3,080,869 A | 3/1963 | Alberts | |
| 3,824,812 A | 7/1974 | Matthews et al. | |
| D281,540 S | 12/1985 | Ternstrom | |
| 5,787,512 A | 8/1998 | Knox | |
| 5,876,392 A | 3/1999 | Hisada | |
| 8,518,008 B2 | 8/2013 | Toshiyasu et al. | |
| 8,555,419 B2 | 10/2013 | Demarest et al. | |
| 9,023,006 B2 | 5/2015 | Shunsuke et al. | |
| 9,358,162 B2 | 6/2016 | Kuwano et al. | |
| 9,827,149 B2 | 11/2017 | LaVon et al. | |
| 10,064,763 B2 | 9/2018 | Takahashi et al. | |
| 10,624,797 B2 | 4/2020 | Morimoto et al. | |
| 2005/0107763 A1 | 5/2005 | Matsuda et al. | |
| 2005/0107764 A1 | 5/2005 | Matsuda et al. | |
| 2006/0036227 A1 | 2/2006 | Hoshino et al. | |
| 2007/0208317 A1 | 9/2007 | Krautkramer et al. | |
| 2008/0161768 A1 | 7/2008 | Baba et al. | |
| 2009/0326504 A1 | 12/2009 | Kaneda | |
| 2011/0251576 A1 | 10/2011 | Ando et al. | |
| 2012/0071852 A1 | 3/2012 | Tsang et al. | |
| 2013/0060219 A1 | 3/2013 | Mukai et al. | |
| 2013/0079742 A1 | 3/2013 | Kuwano et al. | |
| 2013/0110075 A1 | 5/2013 | Mukai et al. | |
| 2013/0123736 A1 | 5/2013 | Ichikawa et al. | |
| 2013/0211363 A1 | 8/2013 | LaVon et al. | |
| 2013/0226127 A1 | 8/2013 | Takahashi et al. | |
| 2013/0331807 A1 | 12/2013 | Ichihara et al. | |
| 2014/0358110 A1 | 12/2014 | Takahashi et al. | |
| 2016/0184145 A1 | 6/2016 | Morimoto | |

FOREIGN PATENT DOCUMENTS

| | | |
|---|---|---|
| CN | 1125622 C | 10/2003 |
| CN | 2668093 Y | 1/2005 |
| CN | 102143729 A | 8/2011 |
| CN | 202699434 U | 1/2013 |
| EP | 2260811 A1 | 12/2010 |
| EP | 2517681 A1 | 10/2012 |
| EP | 2659870 | 11/2013 |
| JP | H0871107 | 3/1996 |
| JP | H9271488 | 10/1997 |
| JP | 2001212176 | 8/2001 |
| JP | 2007029479 | 2/2007 |
| JP | 2007195647 | 9/2007 |
| JP | 2009125087 | 6/2009 |
| JP | 2009153913 A | 7/2009 |
| JP | 2012095937 | 5/2012 |
| JP | 2012135519 | 7/2012 |
| JP | 5566550 | 8/2014 |
| JP | 2014150909 | 8/2014 |
| WO | WO 2013046703 | 4/2013 |
| WO | WO 2016029655 | 3/2016 |

OTHER PUBLICATIONS

P&G AA973MC, All Office Actions for U.S. Appl. No. 15/424,117.
International Search Report and Written Opinion, PCT/CN2015/072193, dated May 27, 2015.
AA00973FM PCT Supplementary International Search Report for PCT/CN2015/072193, dated Jan. 2, 2017, 09 pages.

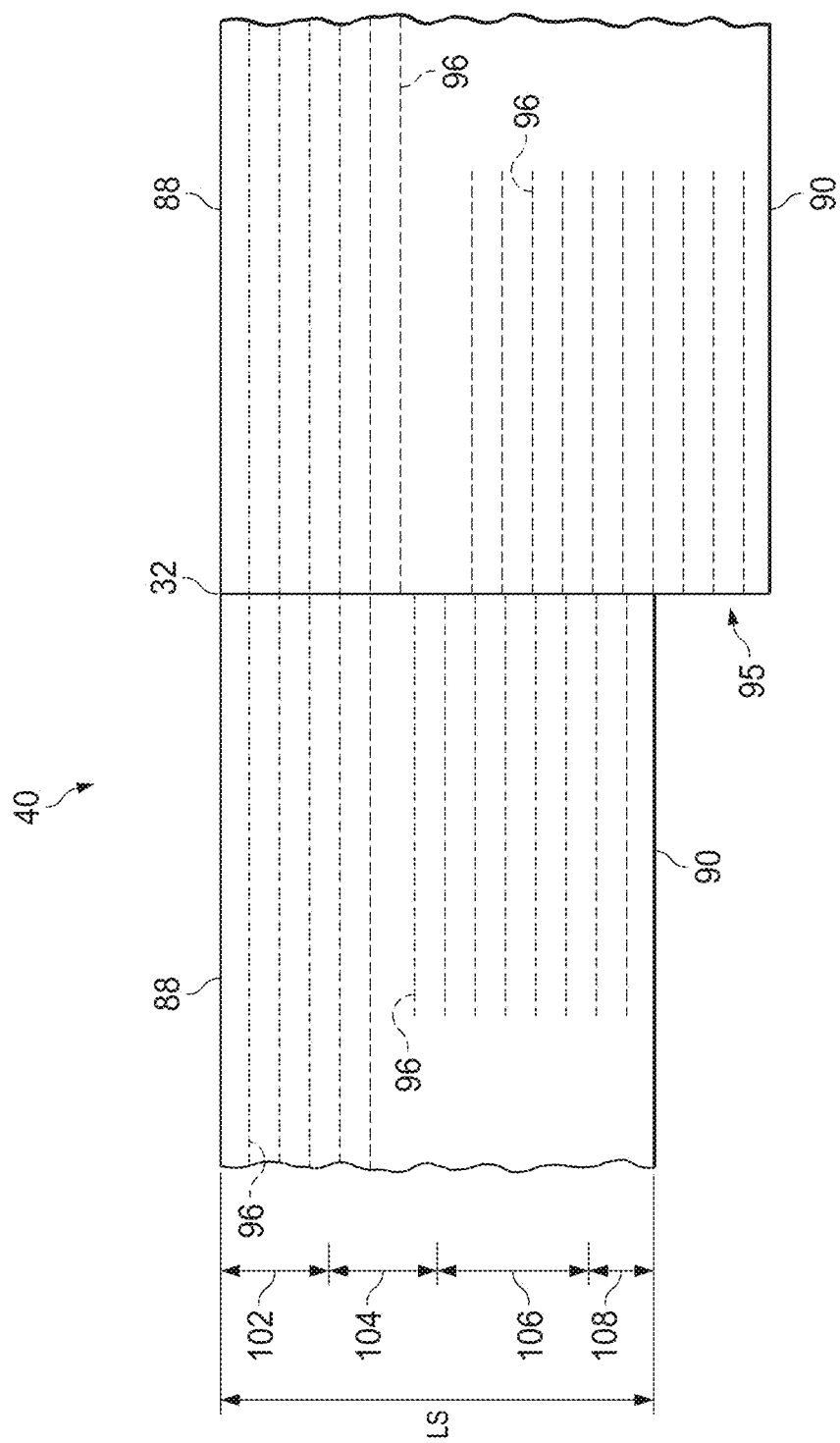

WEARABLE ARTICLE HAVING ELASTIC BELT

CROSS REFERENCE TO RELATED APPLICATIONS

This application is a continuation of U.S. application Ser. No. 15/424,117, filed on Feb. 3, 2017, which is a continuation of Chinese PCT Application No. PCT/CN2015/072193, filed on Feb. 4, 2015, and which is a continuation-in-part of Chinese PCT Application No. PCT/CN2014/085245, filed on Aug. 27, 2014, each of which are herein incorporated by reference in their entirety.

FIELD OF THE INVENTION

The present invention relates to wearable articles having an elastic belt having zones of particular tensile stress profiles.

BACKGROUND OF THE INVENTION

Infants and other incontinent individuals wear wearable articles such as diapers to receive and contain urine and other body exudates. Pull-on wearable articles, or pant-type wearable articles, are those which are donned by inserting the wearer's legs into the leg openings and sliding the article up into position about the lower torso. Pant-type absorbent articles have become popular for use on children who are able to walk and often who are toilet training, as well as for younger children who become more active in movement such that application of taped-type absorbent articles tend to be more difficult.

Many pant-type wearable articles use elastic elements secured in an elastically contractible condition in the waist and/or leg openings. Typically, in order to insure full elastic fit about the leg and the waist such as is provided with durable undergarments, the leg openings and waist opening are encircled at least in part with elasticized elements positioned along the periphery of the respective opening.

Pant-type wearable articles having a main body to cover the crotch region of the wearer and a separate elastic belt defining the waist opening and leg opening are known in the art, such as described in PCT Publication WO 2006/17718A. Such pant-type wearable articles may be referred to as belt-type pants. On the other hand, certain pant-type wearable articles are configured such that the outer cover of the wearable body completely covers the entirety of the garment-facing surface of the article. Such pant-type wearable articles may be referred to as uni-body pants. Belt-type pants, compared to uni-body pants, may be advantageous in having better breathability by having less layers of material in certain areas of the articles, and in that they may be manufactured economically. On the other hand, uni-body pants, compared to belt-type pants, may be advantageous in providing good fit around the leg opening, as uni-body pants may be disposed of elastic members that completely encircle the leg opening. Sag protection and good fit for belt-type pants are mainly provided by the elastic belt. The leg opening of belt-type pants are rendered elastic by the combination of elasticity provided by the main body and the elastic belt. Thus, for belt-type pants, enhancing sag protection and good fit of the leg elastic may compromise comfort around the leg opening. Namely, while providing stronger tensile stress for the elastic belt may enhance sag protection and good fit for the article, such force may also apply to the leg opening and interfere with leg movement, or become a factor of red marking around the front leg opening region. Further, such balancing of sag protection, good fit and comfort around the leg opening should not compromise with good coverage of the buttock area.

Based on the foregoing, there is a need for a pant-type wearable article having balanced performance such as fit, coverage of buttock area, comfort during wear, prevention of sagging, and prevention of leakage. There is further a need for providing such a wearable article in an economical manner.

SUMMARY OF THE INVENTION

The present invention is directed to a wearable article continuous in a longitudinal direction and a transverse direction, comprising a main body and a ring-like elastic belt comprising a front belt and a back belt, the center of the front belt is joined to a front waist panel of the main body, the center of the back belt is joined to a back waist panel of the main body, the front and back belt each having a left side panel and a right side panel where the main body does not overlap, and the transverse edges of the front belt and the back belt are joined by a seam to form a waist opening and two leg openings, wherein each of the front belt and back belt are formed by an inner sheet, an outer sheet, and a plurality of elastic bodies sandwiched therebetween and running in the transverse direction substantially parallel to each other, wherein each front belt and back belt have transversely continuous proximal and distal edges, the proximal edge being located closer than the distal edge relative to the longitudinal center of the article, each front belt and back belt having side edges, wherein:

the entirety of the length of the belt side edge of the front belt is seamed with a certain length of the belt side edge of the back belt to define a seam length LS, the front and back belts each divided into 4 zones extending in the transverse direction and defined by its location from the distal edge to the proximal edge relative to the percentage of the seam length LS wherein; 0-25% is the waist zone, 25-50% is the distal tummy zone, 50-85% is the proximal tummy zone, and 85-100% is the leg zone;

wherein the tensile stress of the front leg zone is no more than 50% of the tensile stress of the front proximal tummy zone, and the tensile stress of the back leg zone is no more than 100% of the tensile stress of the back proximal tummy zone.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings and which like designations are used to designate substantially identical elements, and in which:

FIG. 8 is a schematic side plan view of one embodiment of a wearable article of the present invention in a flat uncontracted condition showing the garment facing surface.

DEFINITIONS

Figure 1:
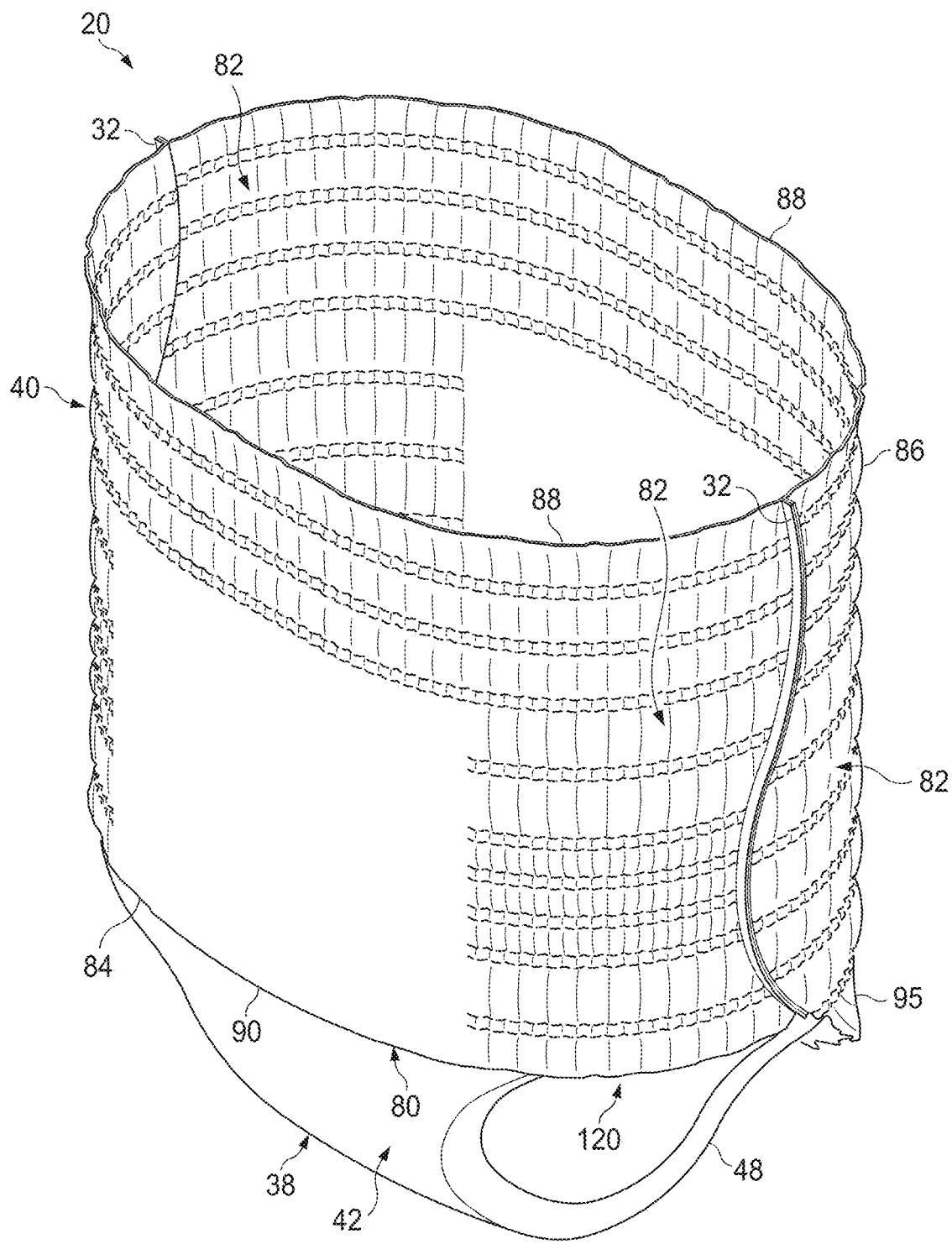
FIG. 1 is a perspective view of one embodiment of a wearable article of the present invention.

As used herein, the following terms shall have the meaning specified thereafter:

"Wearable article" refers to articles of wear which may be in the form of pants, taped diapers, incontinent briefs, feminine hygiene garments, and the like. The "wearable article" may be so configured to also absorb and contain various exudates such as urine, feces, and menses discharged from the body. The "wearable article" may serve as an outer cover adaptable to be joined with a separable disposable absorbent insert for providing absorbent and containment function, such as those disclosed in PCT publication WO 2011/087503A.

"Pant" refers to disposable absorbent articles having a pre-formed waist and leg openings. A pant may be donned by inserting a wearer's legs into the leg openings and sliding the pant into position about the wearer's lower torso. Pants are also commonly referred to as "closed diapers", "prefastened diapers", "pull-on diapers", "training pants" and "diaper-pants."

"Longitudinal" refers to a direction running substantially perpendicular from a waist edge to an opposing waist edge of the article and generally parallel to the maximum linear dimension of the article.

"Transverse" refers to a direction perpendicular to the longitudinal direction.

"Body-facing" and "garment-facing" refer respectively to the relative location of an element or a surface of an element or group of elements. "Body-facing" implies the element or surface is nearer to the wearer during wear than some other element or surface. "Garment-facing" implies the element or surface is more remote from the wearer during wear than some other element or surface (i.e., element or surface is proximate to the wearer's garments that may be worn over the disposable absorbent article).

"Disposed" refers to an element being located in a particular place or position.

"Joined" refers to configurations whereby an element is directly secured to another element by affixing the element directly to the other element and to configurations whereby an element is indirectly secured to another element by affixing the element to intermediate member(s) which in turn are affixed to the other element.

"Extendibility" and "extensible" mean that the width or length of the component in a relaxed state can be extended or increased.

"Elasticated" and "elasticized" mean that a component comprises at least a portion made of elastic material.

"Elongatable material," "extensible material," or "stretchable material" are used interchangeably and refer to a material that, upon application of a biasing force, can stretch to an elongated length of at least about 110% of its relaxed, original length (i.e. can stretch to 10 percent more than its original length), without rupture or breakage, and upon release of the applied force, shows little recovery, less than about 20% of its elongation without complete rupture or breakage as measured by EDANA method 20.2-89. In the event such an elongatable material recovers at least 40% of its elongation upon release of the applied force, the elongatable material will be considered to be "elastic" or "elastomeric." For example, an elastic material that has an initial length of 100 mm can extend at least to 150 mm, and upon removal of the force retracts to a length of at least 130 mm (i.e., exhibiting a 40% recovery). In the event the material recovers less than 40% of its elongation upon release of the applied force, the elongatable material will be considered to be "substantially non-elastic" or "substantially non-elastomeric". For example, an elongatable material that has an initial length of 100 mm can extend at least to 150 mm, and upon removal of the force retracts to a length of at least 145 mm (i.e., exhibiting a 10% recovery).

DETAILED DESCRIPTION OF THE INVENTION

Figure 2:
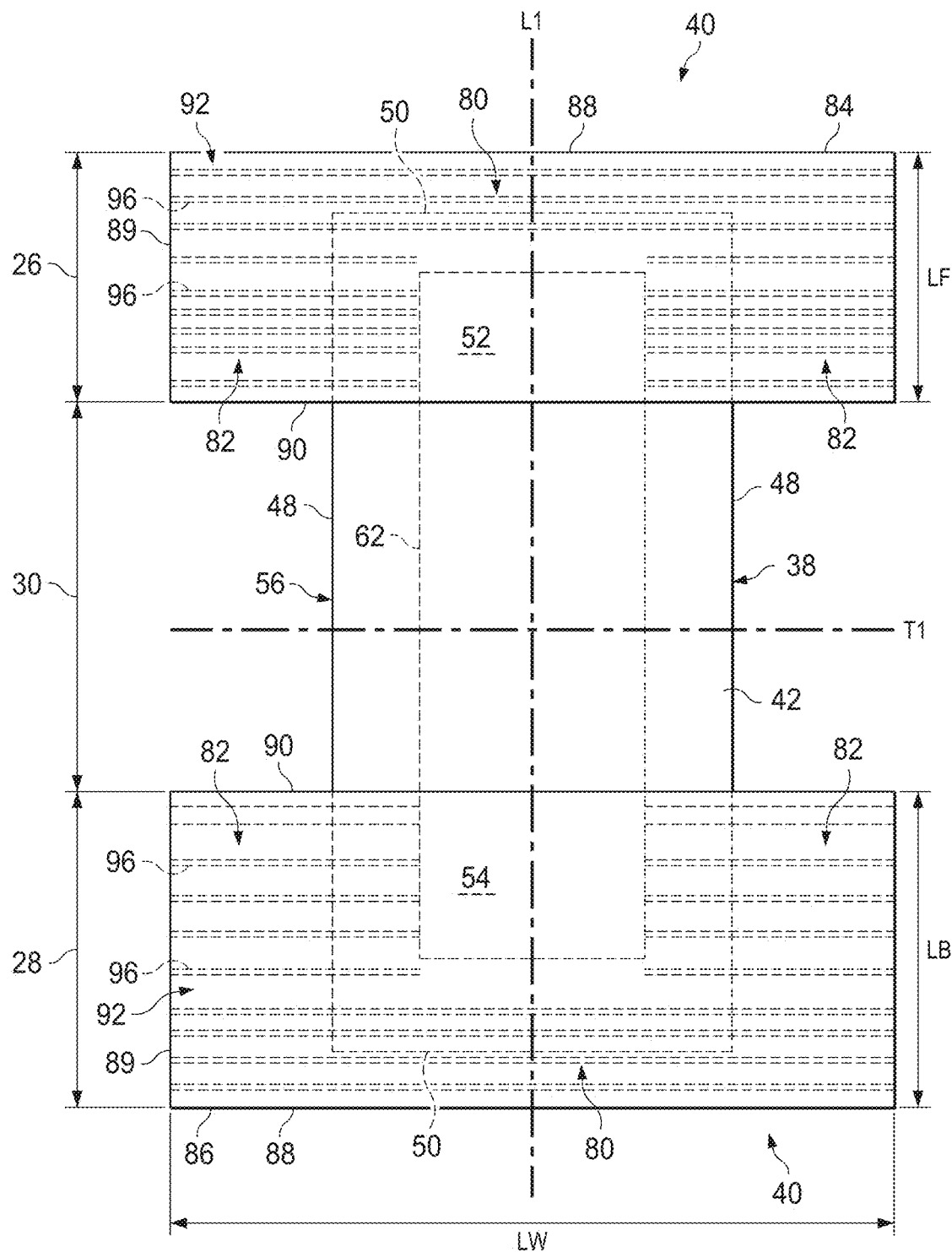
FIG. 2 is a schematic plan view of one embodiment of a wearable article of the present invention with the seams unjoined and removed, and in a flat uncontracted condition showing the garment facing surface.

FIG. 1 is a perspective view of an embodiment of the wearable article 20 of the present invention and FIG. 2 is a schematic plan view of the same article with the seams enjoined and in its flat uncontracted condition showing the garment-facing surface. The wearable article 20 has a longitudinal centerline L1 which also serves as the longitudinal axis, and a transverse centerline T1 which also serves as the transverse axis. The wearable article 20 has a skin-facing surface, a garment-facing surface, a front region 26, a back region 28, a crotch region 30, and seams 32 which join the front region 26 and the back region 28 to form two leg openings and a waist opening. The wearable article 20 comprises a main body 38 to cover the crotch region of the wearer, a front belt 84 and a back belt 86 (hereinafter may be referred to as "front and back belt"), the front and back belts 84, 86 forming a ring-like elastic belt 40 (hereinafter may be referred to as "waist belt") extending transversely defining the waist opening. The front and back belts 84, 86 and the main body 38 jointly define the leg openings.

The main body 38 may contain an absorbent core 62 for absorbing and containing body exudates disposed on the main body 38. In the embodiment shown in FIG. 2, the main body 38 has a generally rectangular shape, left and right longitudinally extending side edges 48 (hereinafter may be referred to as "side edge") and front and back transversely extending end edges 50 (hereinafter may be referred to as "end edge"). The main body 38 also has a front waist panel 52 positioned in the front region 26 of the wearable article 20, a back waist panel 54 positioned in the back region 28, and a crotch panel 56 between the front and back waist panels 52, 54 in the crotch region 30. The center of the front belt 84 is joined to a front waist panel 52 of the main body 38, the center of the back belt 86 is joined to a back waist panel 54 of the main body 38, the front and back belt 84, 86 each having a left side panel and a right side panel 82 where the main body 38 does not overlap.

Referring to FIGS. 1 and 2, the ring-like belt 40 formed by the front belt 84 and back belt 86 acts to dynamically create fitment forces and to distribute the forces dynamically generated during wear. Herein, the term "proximal" is used to indicate the position of a "proximal" portion being closer relative to the longitudinal center of the article, also closer relative to the crotch panel 56 of the main body 38 than the position of a "distal" portion. Therefore, the proximal edge 90 is located closer than the distal edge 88 relative to the crotch panel 56 of the main body 38. The front and back belts 84, 86 may be joined with each other only at the side edges 89 at the seams 32 to form a wearable article having a waist opening and two leg openings. Each leg opening may be provided with elasticity around the perimeter of the leg opening by the combination of elasticity from the front belt 84, the back belt 86, and any from the main body 38. The front leg opening region 120 is disposed adjacent the leg opening along the proximal edge 90 of the left and right side panels 82 of the front belt 84.

The front and back belts 84, 86 are discontinuous with one another in the crotch region 30. In such embodiment, there is no material that covers the entirety of either the wearer-facing surface or garment-facing surface of the article. The front central panel 80 may partly overlap with the front waist panel 52 of the main body 38. The back central panel 80 may partly overlap with the back waist panel 54 of the main body 38. However, the central panels 80 may not extend into the crotch panel 56 of the main body 38 and not be disposed in the crotch panel 56. In the embodiment shown in FIG. 2, the central panels 80 partly overlap with and are joined to the front waist panel 52 and the back waist panel 54, respectively.

Referring to FIG. 2, the front belt 84 and back belt 86 may each comprise an inner sheet 94, an outer sheet 92, (hereinafter also collectively "belt sheets") and a plurality of elastic bodies 96 sandwiched therebetween and running in the transverse direction substantially parallel to each other, and configured to impart elasticity per each zone according to the relationship described below. (The inner sheet 94 is not shown.) Such an article may be economically made.

In one embodiment, the effective transverse width LW of the back belt 86 in the uncontracted condition may be the same as the transverse width of the front belt 84 of the same condition. By "effective transverse width", what is meant is the width available for forming the wearer-facing surface of the article. In one embodiment, each of the proximal edges 90 and the distal edges 88 of the front belt 84 and the back belt 86 may be substantially parallel, as in FIGS. 2 and 7.

In one embodiment, the longitudinal length LB of the back belt 86 between the back distal edge 88 and the back proximal edge 90 along its entire width LW of the back belt 86 may be approximately the same as the longitudinal length LF of the front belt 84 between the front distal edge 88 and the front proximal edge 90. In such embodiment, the seams 32 close the front and back belt 84, 86 side edges 89 of the same length for forming the article. Such an article may be economically made.

Figure 3:
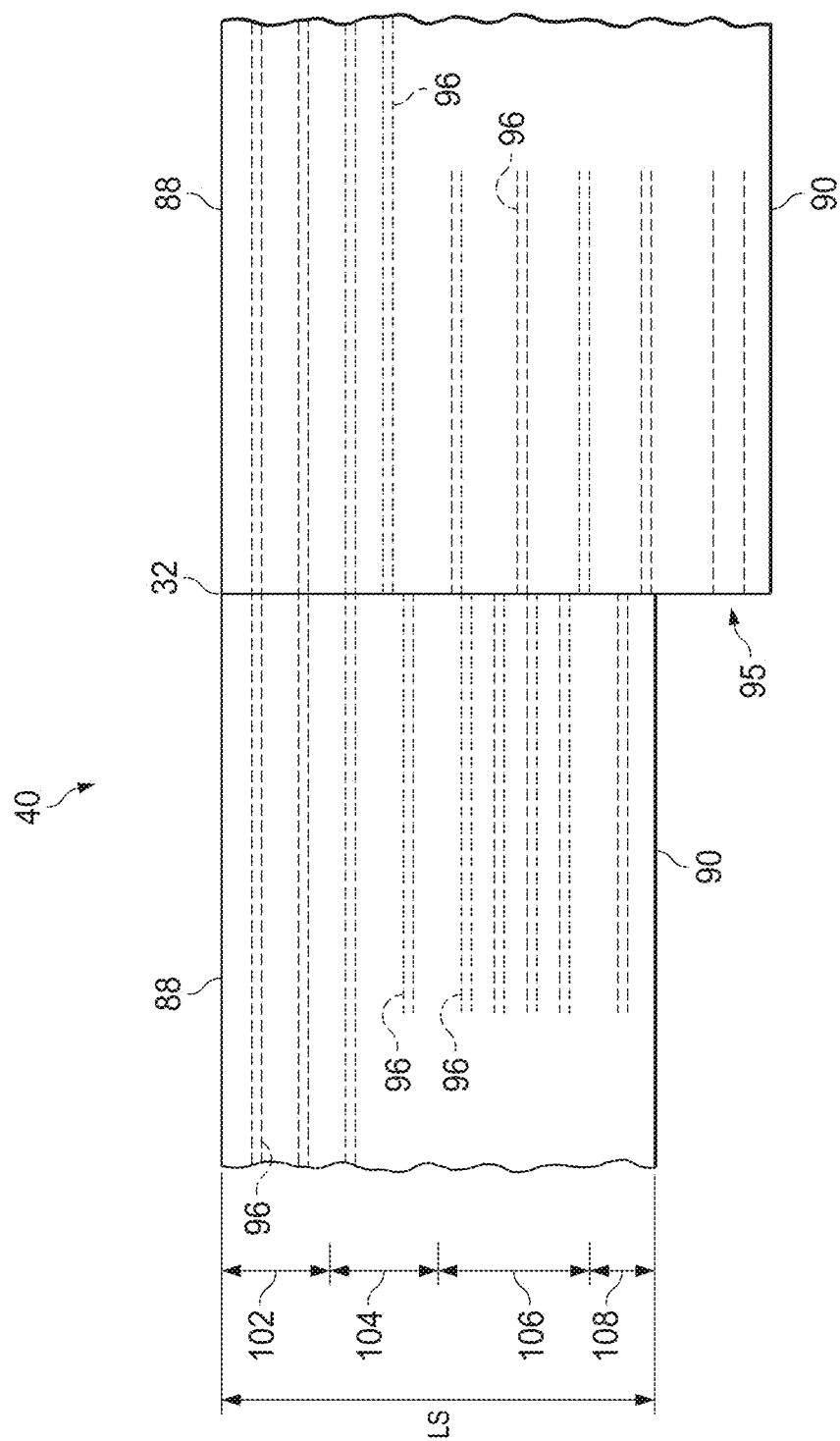
FIG. 3 is a schematic side plan view of one embodiment of a wearable article of the present invention in a flat uncontracted condition showing the garment facing surface.

In one embodiment, the back belt 86 may have a greater longitudinal length LB between the back distal edge 88 and the back proximal edge 90 along its entire width LW of the back belt 86 in the transverse direction than the longitudinal length LF of the front belt 84 between the front distal edge 88 and the front proximal edge 90 (FIGS. 1-3). In such embodiment, when the wearable article is assembled to form the waist opening and the leg openings, the wearable article 20 is folded along the transverse centerline T1 such that the front distal edge 88 is aligned with the back distal edge 88. The front side edge 89 is also aligned with a portion of the back side edge 89. Then the front belt 84 and the back belt 86 are joined at the front and back side edges 89 at the seams 32. The front and back proximal edges 90, however, may not be aligned to one another. The back proximal edge 90 may be disposed longitudinally closer than the front proximal edge 90 relative to the transverse center line T1 such that the proximal portion of the back side panel 82 extends toward the crotch panel 56 of the main body 38 beyond the front proximal edge 90. The side edge of the proximal portion of the back side panel 82 may not be joined to anywhere and free from attachment. Thus, the proximal portion of the back side panel 82 provides a buttock cover 95 as in FIG. 1.

Whether or not the longitudinal length LB of the back belt 86 and the longitudinal length LF of the front belt 84 are the same, the entirety of the longitudinal length LF of the belt side edge 89 of the front belt 84 is seamed with the belt side edge 89 of the back belt 86 to define a seam length LS, as in FIG. 3. When the front belt 84 has straight distal edges 88 and proximal edges 90 that are substantially parallel of each other, then the longitudinal length LF of the front belt 84 is equal to the seam length LS.

In one embodiment, the outer sheet 92 of the front or back belt 84, 86 towards the distal edge 88 may be longer than the size of the inner sheet 94 in the longitudinal direction, and an end flap of the outer sheet 92 may be folded over the distal end of the inner sheet 94 at the waist opening. The front and back belts 84, 86 may be provided in low caliper non-woven material for sake of breathability and softness of the belt 40.

The tensile stress (N/m) of the front and back elastic belts 84, 86, respectively, may be profiled in order to provide the benefits of the present invention. The tensile stress may be measured, for example, by the Belt Zone Tensile Stress Measurement described herein below. When the elasticity of the front and back elastic belts 84, 86 are provided by a plurality of elastic bodies 96 running in the transverse direction, the tensile stress may be adjusted by one or more of the following methods; 1) elongation rate of the elastic body 96; 2) density (dtex) of the elastic body 96; 3) longitudinal interval of multiple elastic bodies 96; and 4) effective length of elasticity of the elastic body 96 in the transverse direction. By elongation, "0% elongation" is meant the original length of the elastic body. When a portion of an elastic body is removed of its elasticity, the remainder of the intact elastic body capable of imparting elasticity is defined as the "effective length of elasticity of an elastic body". The elastic bodies 96 disposed on the front and/or back belt 84, 86 may be treated such that certain of the area overlapping the front and/or back waist panels 52, 54 of the main body 38 are removed of elasticity. Removal of elasticity from at least a portion of the area overlapping the front and/or back waist panel 52, 54 of at least one elastic body may be advantageous when the main body 38 comprises an absorbent core 62, in that elasticity in the front and/or back area may cause bunching of the absorbent core 62 and interfere with close fit of the main body 38 to the wearer. In one embodiment, at least a portion of, or at least 10% of, or at least 20% of, or at least 30% of, the elasticity of; at least one of, or at least half of, or at least two thirds of, or all of, the elastic bodies are removed in the region overlapping with the front and back waist panels 52, 54 or the absorbent core 62 of the main body 38.

Referring to FIG. 3, the front and back belts 84, 86 are each divided into 4 zones extending in the transverse direction and defined of its position from the distal edge 88 to the proximal edge 90 relative to the percentage of the seam length LS. The entirety of the length of the belt side edge 89 of the front belt 84 is seamed with a certain length of the belt side edge 89 of the back belt 86 to define a seam length LS. When seam length LS is considered 0% at the distal edge 88 and 100% at the proximal edge 90 of the front belt 84, the zones are defined as such: 0-25% is the waist zone 102, 25-50% is the distal tummy zone 104, 50-85% is the proximal tummy zone 106, and 85-100% is the leg zone 108. When there is an elastic body disposed at 25% from the distal edge 88, such elastic body is considered to be included in the waist zone 102. When there is an elastic body disposed at 50% from the distal edge 88, or 85% from the distal edge 88, such elastic body is considered to be included in the proximal tummy zone 106. For embodiments where the back belt 86 has a greater longitudinal length LB than the longitudinal length LF of the front belt 84, the remaining length of "LB minus LS" of the back belt 86 is not counted in the 4 zones described above.

In the article of the present invention, the tensile stress of the front leg zone 108 may be no more than 50%, or no more than 40% of the tensile stress of the front proximal tummy zone 106. The elastic bodies disposed on the front leg zone 108 may have a density of no more than 680 dtex, or from 340 to 680 dtex, or from 480 to 680 dtex. The elastic bodies are disposed on the front leg zone at an elongation of no more than 300%, or no more than 200%, or from 110-180%. In one embodiment, regardless of the density of the elastic body to be used, when the elastic bodies of the front leg zone 108 are disposed at a first elongation and the elastic bodies of the front proximal tummy zone 106 are disposed at a second elongation, the difference in percentage number of the first and second elongation may be adjusted to be no more than 200. By keeping the elongation percentage number difference to no more than 200, or no more than 150, or no more than 100, a front proximal tummy to leg opening area with suitable aesthetics may be made.

The tensile stress of the back leg zone 108 may be no more than 100%, or no more than 60% of the tensile stress of the back proximal tummy zone 106. Further, the tensile stress of the front proximal tummy zone 106 may be no less than the back proximal tummy zone 106, or no less than 150%, or no less than 170%, or no less than 190%, of the back proximal tummy zone 106. There may be no more than 18, or from 8 to 18 elastic bodies disposed on the front proximal tummy zone 106. The elastic bodies disposed on the front proximal tummy zone 106 may have a density of no less than 540 dtex, or no less than 680 dtex, or no less than 940 dtex.

Figure 4:
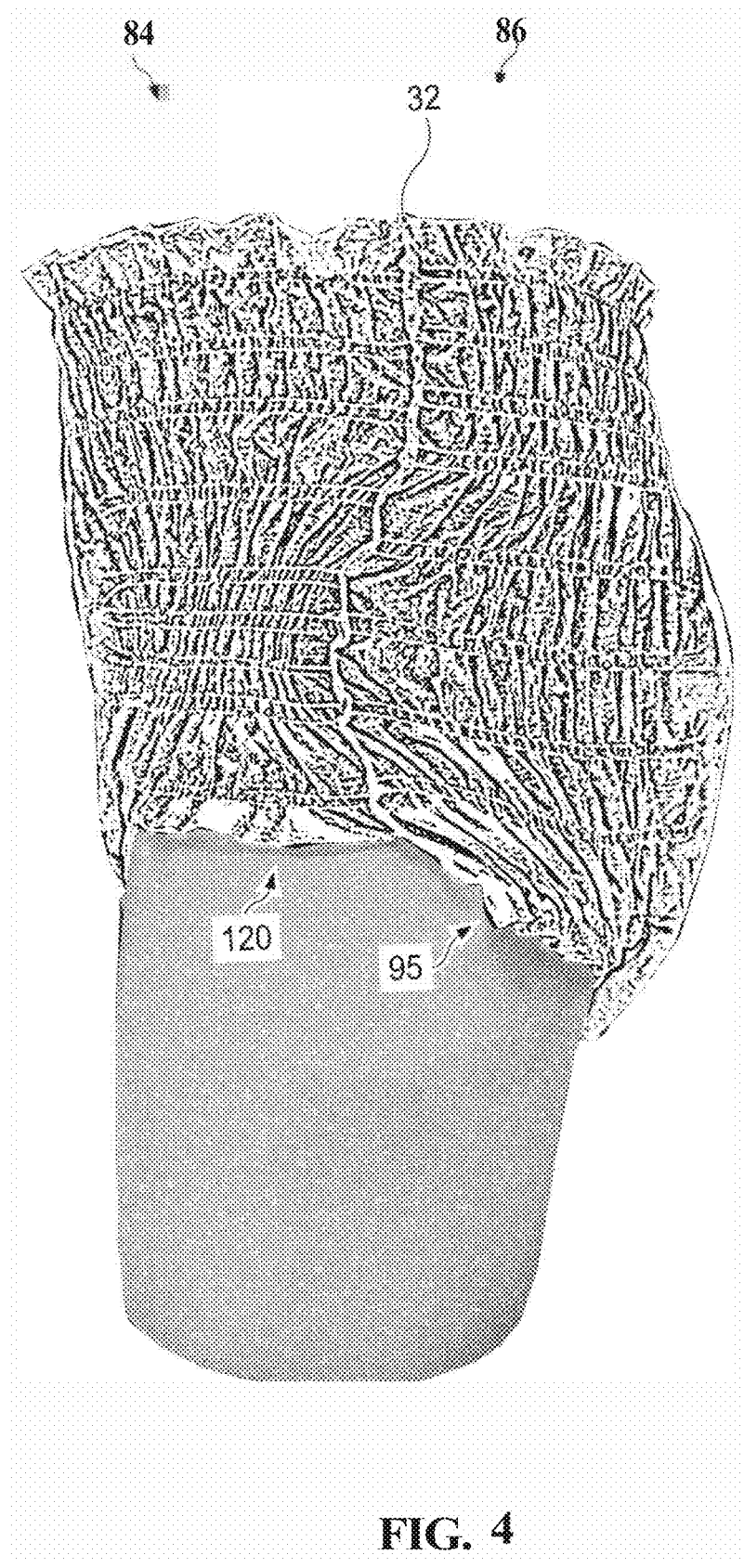
FIG. 4 is a side view of one embodiment of a wearable article of the present invention worn on a mannequin.
Figure 5:
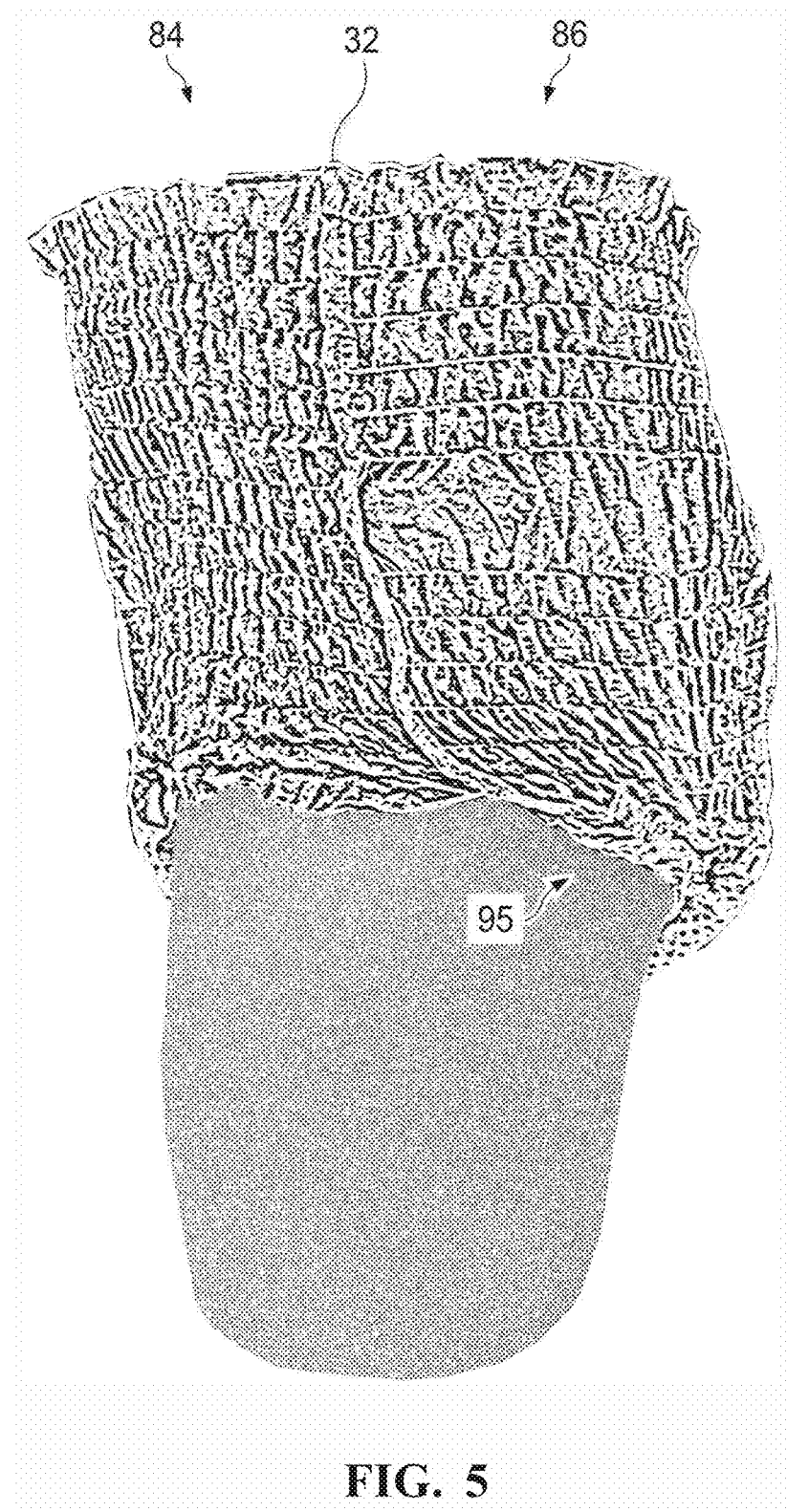
FIG. 5 is a side view of a wearable article of the prior art worn on a mannequin.

Without being bound by theory, such profiling per zone is believed to provide the article of the present invention with sag protection, good fit and comfort around the leg opening, by anchoring the article mainly at the trochanter of the wearer, while facilitating leg movement. The front proximal tummy zone 106 more or less matches with the trochanter of the wearer when worn. As long as the article is anchored securely at the trochanter, the leg zone 108 adjacent the leg opening may be provided with significantly less tensile stress compared to the proximal tummy zone 106. Thus, the soft fit at the front leg opening region 120 facilitates leg movement. Further, such profiling per zone provides better conforming of the waist belt 40 to a human body, particularly to a lower torso of a child of less than 36 months of age. By gathering the waist belt area around the front proximal tummy zone 106, while leaving relatively more area around the back proximal tummy zone 106 and the back leg zone 108, the article better conforms to the shape of the buttock of the wearer when worn. For embodiments where the buttock cover 95 is created by the proximal edge 90 of the back waist belt 86, providing the front and back leg zones 108 with more or less similar tensile stress profile, coupled with the conforming to the wearer in the buttock, allows the buttock cover 95 to cover the lower end of the buttock in a natural manner. FIG. 4 shows a side view of one embodiment of an article of the present invention when worn on a mannequin. As can be seen in FIG. 4, the article may be configured to conform to the lower torso better than that of the prior art as shown in FIG. 5.

The elastic profiling described herein may be utilized for economically making an article of no less than 420 mm, or no less than 450 mm, or no less than 500 mm in the longitudinal axis by using a total of no more than 60, or no more than 46 elastic bodies for the elastic belt 40 per article. The article of the present invention may have an entire longitudinal length of the article of from 350 mm to 600 mm, an effective transverse belt width (LW) of from 315 mm to 500 mm, a back belt longitudinal length (LB) of from 100 mm to 180 mm, a front belt longitudinal length (LF) of from 80 mm to 160 mm, a main body longitudinal length of from 310 mm to 560 mm, and a main body transverse width of from 150 mm to 210 mm. The article of the present invention may have a distance between the distal edge of the front belt to the longitudinal edge of the main body of from 0 mm to 70 mm, and a distance between the distal edge of the back belt to the longitudinal edge of the main body of from 0 mm to 90 mm, and such distances on the front and back belt may be the same or different. The longitudinal length of the main body may be from 70% to 100% of the entire longitudinal length of the article. When the main body comprises an absorbent core 62, the core may have a longitudinal length of from 270 mm to 500 mm, a maximum transverse width of the core of from 90 mm to 125 mm, and a distance between the longitudinal edge of the core to the longitudinal edge of the main body of from 10 mm to 40 mm. The longitudinal length of the core may be from 60% to 95% of the entire longitudinal length of the article, or from 66% to 97% of the main body.

The article of the present invention may have a Waist Circumference Force provided by the elastic bodies 96 disposed on the waist belt 40 of no more than 10 N, or no more than 8 N, according to the Whole Article Force Measurement as described herein below. The Whole Article Force Measurement is for quantifying the force provided by the article 20 when stretched along the waist circumference, simulating initial stretch experience of the article 20 in the transverse direction when the user inserts hands in the article and expands the article. Namely, more or less the total tensile force provided by the elastic bodies 96 disposed in the transverse direction are measured. While there may be other elastic bodies disposed on the article, for example along the longitudinal side edges of the main body, the impact of such other elastic bodies are known to be small, when the user stretches the article in the transverse direction. The Whole Article Force Measurement is obtained by extending, or loading, the article in the transverse direction until a force of 19.6 N is attained, wherein the force at the point where the belt 40 article reaches 70% of the maximum stretch is obtained. The force expected to be perceived by the user for expanding the article may be controlled, such that the user may experience a satisfying expansion of the belt 40 without excess effort.

The obtained wearable article of the present invention may provide fit, coverage of buttock area, comfort during wear, prevention of sagging, and prevention of leakage. The obtained wearable article of the present invention may be made in an economical manner.

Whole Article Force Measurement

Force is measured using an Electronic Tensile Tester with a computer interface such as the MTS Criterion C42 running TestWorks 4 Software (available from MTS SYSTEMS (CHINA) CO., LTD) or equivalent instrument. A load cell is selected so that force results for the samples tested will be between 10 and 90% of capacity of the load cell used. The instrument is calibrated according to the manufacturer's instructions. All testing is performed in a room maintained at 23±2° C. and 50±5% relative humidity.

Figure 6:
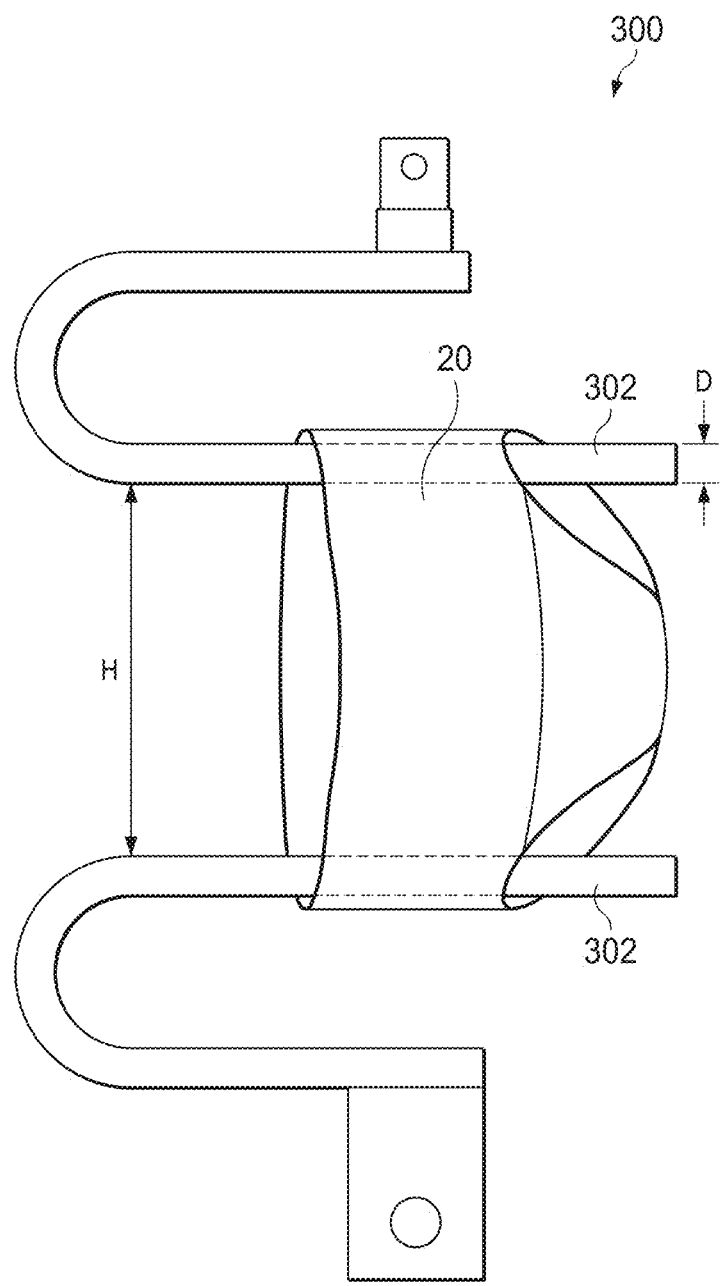
FIG. 6 is a schematic view of an example of a hanger-type sample holding fixture according to the "Whole Article Force Measurement".

The tensile tester is fitted with hanger-type sample holding fixtures 300 as shown in FIG. 6. Each fixture comprises a rigid linear rubber-coated horizontal bar section 302 to prevent sample slippage during testing. The outer bar diameter (including the rubber coating) of the horizontal bar sections is 10.0 mm. The central axes of the horizontal bar sections 302 are configured to remain parallel and in the same vertical plane throughout the test procedure. The gauge circumference is determined by the following equation:

Gauge Circumference=$2\times(H+D+\pi D/2)$ where H is the vertical gap between the horizontal bar sections 302, and D is the outer diameter of the bar.

The instrument is set up to go through the following steps:

| | |
|---|---|
| Crosshead Speed | 254.0 mm/min |
| Final Load Point | 19.61 N |
| Hold Time | 0 |
| Number of Cycles | 1 |
| Data Acquisition Rate | 50 Hz |

A sample article 20 is inserted onto the upper horizontal bar section 302 so that the bar passes through the waist opening and one leg opening of the article. The crosshead is raised until the specimen hangs above the lower bar and does not touch lower bar 302. The load cell is tared and the crosshead is lowered to enable the lower bar 302 to be inserted through the waist opening and other leg opening without stretching the article. The article is adjusted so that the longitudinal centerline L1 of the article is in a horizontal plane halfway between the upper and lower bars 302. The center of the side portion in contact with the bar 302 is situated on the same vertical axis as the instrument load cell. The crosshead is raised slowly while the article is held in place by hand as necessary until the force is between 0.05 and 0.1 N, while taking care not to add any unnecessary force. The gauge circumference at this point is the Initial Gauge Circumference. The test is initiated and the crosshead moves up at 254 mm/min until a force of 19.6 N is attained, then the crosshead immediately returns to the initial gauge circumference at the same speed. The maximum circumference at 19.6 N and the force at 70% stretch circumference during the extension segment of the test are recorded.

Circumference (mm)=$2\times(H+D+\pi D/2)$

The maximum circumference at 19.6 N is defined as the Full Stretch Circumference (mm). The 70% stretch circumference is defined as the full stretch circumference×0.7. The Waist Circumference Force is defined as the force at 70% stretch circumference during the load (extension) segment of the test.

Five samples are analyzed and their average Initial Gauge Circumference, average Full Stretch Circumference and average Waist Circumference Force are calculated and reported to the nearest 1 mm, 1 mm and 0.01 N, respectively.

Belt Zone Tensile Stress Measurement

The tensile stress (N/m) is calculated by tensile force (N) divided by the specimen width (m). Force may be measured using an Electronic Tensile Tester with a computer interface such as the MTS Criterion C42 running TestWorks 4 Software (available from MTS SYSTEMS (CHINA) CO., LTD) or equivalent instrument. A load cell is chosen so that force results for the samples tested will be between 10 and 90% of capacity of the load cell. The instrument is calibrated according to the manufacturer's instructions. All testing is performed in a room maintained at 23±2° C. and 50±5% relative humidity. The instrument is equipped with single line contact grips at least as wide as the test specimen.

To obtain test specimens, the sample article is cut open along the side seams 32, and the front and rear elastic belt sections 40 are removed from the main body 38 by separating the bonding between the waist belt and main body. Cold Spray may be used, paying attention not to make wrinkles in the belt sections. Care is taken not to spray on any belt elastic body 96. The obtained elastic belts 40 are severed into zones 102, 104, 106, 108 according to the present invention with care not to cut any elastic body 96. Samples are pre-conditioned at 23° C.±2 C.° and 50%±5% relative humidity for two hours prior to testing.

The instrument is set up to go through the following steps. Initial Gauge Length is calculated from the Initial Gauge Circumference which is determined during the Whole Article Force Test using separate identical articles, as described above. Initial Gauge Length=0.5×Initial Gauge Circumference. The final gauge length is calculated from the Full Stretch Circumference which is determined during the Whole Article Force Test, as described above.

| | |
|---|---|
| Crosshead Speed | 254.0 mm/min |
| Data Acquisition Rate | 50 Hz |
| Final Gauge Length | 0.5 × Full Stretch Circumference |
| Hold Time | 0 |
| Number of Cycles | 1 |

One end of the specimen is clamped into the upper clamp and the load is tared. The other end of the specimen is clamped into the lower clamp. Approximately 5 mm of each end of the specimen is behind the contact line of the grip. The test is started and the specimen is extended to the final gauge length at a crosshead speed of 254 mm/min, then immediately returned to the original gauge length at the same speed. The specimen is extended in the article transverse direction during the test. The unload force at 70% of the Final Gauge Length during the unload segments of the test is recorded.

Five articles are analyzed and the unload forces are recorded for each of the front and back zones 102, 104, 106, 108. The average tensile force (N) is calculated to the nearest 0.01 N for each zone including the front and back specimens for that zone. The tensile stress for each zone is calculated by the average tensile force (N) divided by the average specimen width (m) and reported to the nearest 0.1 N/m.

EXAMPLES

Example 1

A wearable article of the present invention having an elastic profiling according to FIGS. 2, 3, and Table 1 below having an effective belt width LW of 355 mm and a seam length LS of 130 mm.

Examples 2-4

Figure 7:
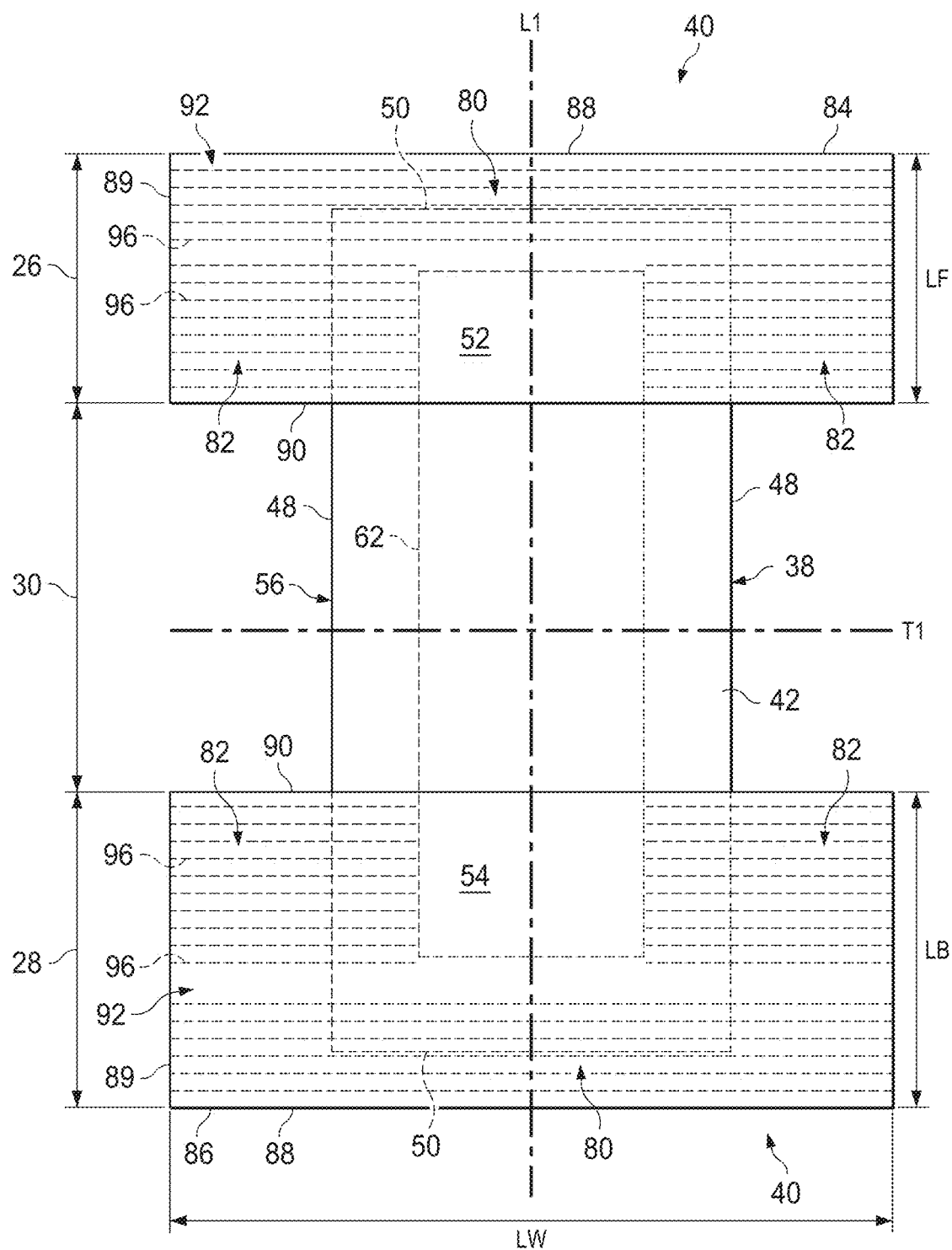
FIG. 7 is a schematic plan view of one embodiment of a wearable article of the present invention with the seams unjoined and removed, and in a flat uncontracted condition showing the garment facing surface.

A wearable article of the present invention having an elastic profiling according to FIGS. 7, 8, and Table 1 below having an effective belt width LW of 355 mm and a seam length LS of 130 mm.

Comparative Example 1

A wearable article of the prior art having an elastic profiling according to FIGS. 7, 8, and Table 1 below having an effective belt width LW of 355 mm and a seam length LS of 130 mm.

TABLE 1 dtex/elongation %/number of elastic bodies

| | Example 1 | Example 2 | Example 3 | Example 4 | Comparative Example |
|---|---|---|---|---|---|
| Front proximal tummy zone | 540 dtex/ 275%/2 and 940 dtex/ 275%/6 | 680 dtex 275% 5 | 680 dtex 275% 5 | 680 dtex 275% 5 | 680 dtex 275% 5 |
| Front leg zone | 540 dtex 275% 2 | 540 dtex 182% 2 | 470 dtex 150% 2 | 680 dtex 200% 2 | 680 dtex 275% 2 |
| Back proximal tummy zone | 540 dtex 275% 6 | 680 dtex 275% 4 | 680 dtex 275% 4 | 680 dtex 275% 4 | 680 dtex 275% 4 |
| Back leg zone | 540 dtex 275% 2 | 540 dtex 182% 3 | 470 dtex 150% 3 | 680 dtex 182% 3 | 680 dtex 275% 3 |

All elastics are removed of elasticity at the central area of the central panels 80 overlapping with the main body 38, and have 66% effective length of elasticity.

The Waist Circumference Force and tensile stress for each zone were measured according to the Whole Article Force Measurement and Belt Zone Tensile Stress Measurement methods herein, respectively, for Example 1 and Comparative Example 1. Results are found in Table 2.

TABLE 2

| | Example 1 | Comparative Example 1 |
|---|---|---|
| Waist Circumference Force (N) | 6.12 | 5.99 |
| Tensile Stress (N/m) | | |
| Front proximal tummy zone | 107.7 | 25.7 |
| Front leg zone | 19.5 | 22.1 |
| Back proximal tummy zone | 32.5 | 20.4 |
| Back leg zone | 20.5 | 23.1 |

For Examples 1-4, the tensile stress of the front leg zone 108F is no more than 40% of the tensile stress of the front proximal tummy zone 106F. For Comparative Example 1, the tensile stress of the front leg zone 108F exceeds 50% of the tensile stress of the front proximal tummy zone 106F.

For Examples 1-4, the tensile stress of the back leg zone 108B is less than the tensile stress of the back proximal tummy zone 106B. For Comparative Example 1, the tensile stress of the back leg zone 108B is greater than the tensile stress of the back proximal tummy zone 106B.

Example 1 provided profiling of tensile stress per zone without significant increase of total tensile force of the belt compared to Comparative Example 1.

Compared to Comparative Example 1, Example 1 provides improvement in one or more of: fit, coverage of buttock area, comfort during wear, prevention of sagging, fit around legs, prevention of red mark around legs, and prevention of leakage.

Consumer Acceptance

Example 1 and Comparative Example 1 including an identical absorbent core were subjected to a consumer test for application on 50 panelists and 51 panelists, respectively. The panelists were caregivers of Japanese Size 4 (L-size) wearers of age 0-36 months, and at about the same boy/girl ratio. The caregivers of the panelists were given enough products to use either product for 5 days, and then answer a questionnaire including the following questions, and asked to rate the performance in 5 scales from "Very Poor" to "Excellent", wherein 100 represents "Excellent", 75 represents "Good", 50 represent "Fair", 25 represent "Poor" and 0 represents "Very Poor". The ratings were averaged and statistically analyzed. Test results are shown below in Table 3.

TABLE 3

| Question | Example 1 | Comparative Example 1 |
|---|---|---|
| Overall Rating | 77* | 69 |
| Overall Fit Of The Pant When The Diaper Is Full | 72 | 64 |
| Preventing Skin Problems Such As Rash/Redness/Would Cause You Concern | 70 | 62 |
| Preventing Diaper Dropping & Sagging That Would Cause You Concern | 76 | 71 |

*Statistically significant over Comparative Example 1 with 90% confidence level

According to the consumer acceptance test results, Example 1 of the present invention, compared to Comparative Example 1, was accepted better in all aspects of the product listed above, and was statistically significantly better accepted in "Overall Rating".

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A wearable article comprising a main body and an elastic belt comprising a front belt and a back belt, the main body being continuous with the front belt and the back belt, and the transversely opposed side edges of the front belt and the back belt are joined to form laterally opposed side seams such that a waist opening and two leg openings are formed;

wherein each of the front belt and back belt are formed by an inner sheet, an outer sheet, and a plurality of elastic bodies sandwiched therebetween;

wherein at least some of the elastic bodies run in the transverse direction substantially parallel to each other;

wherein each front belt and back belt have transversely continuous proximal and distal end edges, the proximal edge being located closer than the distal edge relative to a transverse center axis of the article;

wherein an entire length of the transverse edge of the front belt is seamed with less than an entire length of the transverse edge of the back belt to define a seam length LS;

wherein the front and back belts are each divided into 4 zones extending in the transverse direction and each zone being defined by its location from the distal edge to the proximal edge relative to the percentage of the seam length LS wherein; 0-25% is a waist zone, 25-50% is a distal tummy zone, 50-85% is a proximal tummy zone, and 85-100% is a leg zone; and wherein the tensile stress of the back belt leg zone is no more than 100% of the tensile stress of the back belt proximal tummy zone.

2. The article of claim 1, wherein the elastic bodies disposed in the front belt leg zone have a density of no more than 680 dtex.

3. The article of claim 2, wherein the elastic bodies in the front belt leg zone are disposed at an elongation of no more than 300%.

4. The article of claim 1, wherein the tensile stress of the front belt leg zone is no more than 40% of the tensile stress of the front belt proximal tummy zone.

5. The article of claim 1, wherein no more than 18 elastic bodies are disposed in the front belt proximal tummy zone.

6. The article of claim 5, wherein the elastic bodies disposed in the front belt proximal tummy zone have a density of no less than 540 dtex.

7. The article of claim 1, wherein the elastic bodies of the front belt leg zone are disposed at a first elongation and the elastic bodies of the front belt proximal tummy zone are disposed at a second elongation, the difference in elongation percentage number of the first and second elongations being no more than 200.

8. The article of claim 1, wherein the front and back belts comprise no more than 60 elastic bodies in total.

9. The article of claim 1, wherein the article has a Waist Circumference Force according to the Whole Article Force Measurement herein of no more than 10 N.

10. The article of claim 1, wherein the length of the article along a longitudinal axis is no less than 420 mm.

11. The article of claim 1, wherein each of the proximal end edges and the distal end edges of the front belt and the back belt are substantially parallel.

12. The article of claim 11, wherein a longitudinal length of the back belt is longer than a longitudinal length of the front belt, and wherein the distal end edge of the front belt is aligned with the distal end edge of the back belt, and the proximal end edge of the front belt is not aligned with the proximal end edge of the back belt.

13. The article of claim 1, wherein at least a portion of the elasticity of at least one of the elastic bodies is removed in the region overlapping with the front and back waist panels of the main body.

14. The article of claim 1, wherein the main body comprises an absorbent core and wherein the plurality of elastic bodies of the front and back belts do not overlap the absorbent core.

15. The article of claim 1, wherein at least some of the plurality of elastic bodies of the front belt substantially meet the plurality of elastic bodies of the back belt at the transversely opposed side edges of the front and back belts at the side seam in the waist zone.

16. The article of claim 15, the plurality of elastic bodies of the front belt do not meet the plurality of elastic bodies of the back belt at the transversely opposed side edges of the front and back belts at the side seam in the distal tummy zone.

17. The article of claim 16, the plurality of elastic bodies of the front belt do not meet the plurality of elastic bodies of the back belt at the transversely opposed side edges of the front and back belts at the side seam in the distal proximal zone.

18. The article of claim 17, the plurality of elastic bodies of the front belt do not meet the plurality of elastic bodies of the back belt at the transversely opposed edges of the front and back belts at the side seam in the distal leg zone.

19. The article of claim 1, wherein a portion of the transversely opposed side edge of the back belt that is not seamed with the transversely opposed side edge of the front belt form a buttocks cover region, wherein the buttocks cover region comprises at least two elastic bodies.

20. The article of claim 1, wherein the waist zone comprises at least three elastic bodies in the front belt and at least three elastic bodies in the back belt.

* * * * *